United States Patent [19]

Eisenhart et al.

[11] Patent Number: 5,266,646

[45] Date of Patent: Nov. 30, 1993

[54] MULTI-STAGE POLYMER PARTICLES HAVING A HYDROPHOBICALLY-MODIFIED, IONICALLY-SOLUBLE STAGE

[75] Inventors: Eric K. Eisenhart, Doylestown; Dennis P. Lorah, Lansdale; Susan R. Gill, Lansdale; Eric A. Johnson, Lansdale, all of Pa.

[73] Assignee: Rohm and Haas Company, Philadelphia, Pa.

[21] Appl. No.: 933,970

[22] Filed: Aug. 24, 1992

Related U.S. Application Data

[63] Continuation of Ser. No. 352,226, May 15, 1989, abandoned.

[51] Int. Cl.$^5$ .................. C08F 265/04; C08F 265/06
[52] U.S. Cl. .................... 525/301; 525/902; 525/302; 525/303; 525/64
[58] Field of Search .............. 525/301, 302, 303, 64, 525/902

[56] References Cited

U.S. PATENT DOCUMENTS

| | | | |
|---|---|---|---|
| 4,075,411 | 2/1978 | Dickstein | 525/902 |
| 4,427,836 | 8/1984 | Kowalski et al. | 525/902 |
| 4,453,261 | 6/1984 | Waite et al. | 525/243 |
| 4,468,498 | 1/1984 | Kowalski et al. | 525/901 |
| 4,469,825 | 9/1984 | Kowalski et al. | 525/902 |
| 4,594,363 | 6/1986 | Blankenship et al. | 525/902 |
| 5,021,469 | 6/1991 | Langerbeins et al. | 525/902 |

FOREIGN PATENT DOCUMENTS 3902103 8/1990 Fed. Rep. of Germany .

*Primary Examiner*—James J. Seidleck
*Assistant Examiner*—W. R. H. Clark
*Attorney, Agent, or Firm*—Marvin J. Powell

[57] ABSTRACT

Multi-stage polymer particles comprising at least one hydrophobically-modified, ionically-soluble polymer stage polymerized from a) hydrophobic monomer, b) ethylenically-unsaturated, ionizable monomer, c) nonionic, ethylenically-unsaturated monomer and optionally d) multi-functional compound are improved thickeners.

22 Claims, No Drawings

MULTI-STAGE POLYMER PARTICLES HAVING A HYDROPHOBICALLY-MODIFIED, IONICALLY-SOLUBLE STAGE

This application is a continuation of application Ser. No. 352,226, filed May 15, 1989, now abandoned.

SUMMARY OF THE INVENTION

This invention relates to polymer particles comprising two or more polymer stages wherein:
1) At least one of said polymer stages is an ionically-soluble polymer, said ionically-soluble polymer being polymerized from a monomer mixture comprising;
   a) about 0.1 to about 55% by weight hydrophobic monomer having the formula;

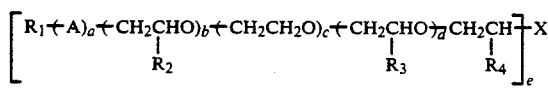

where A is $-O-$, $-S-$, $-\underset{R_5}{N}-$, $-\underset{O}{\overset{\|}{C}}-\underset{R_5}{N}-$, $-\underset{O}{\overset{\|}{C}}-O-$ or $$-O-\underset{O}{\overset{\|}{C}}-O-;$$

$R_1$ and $R_5$ independently are $(C_1-C_{30})$ alkyl, a (mono-, di-, or tri) $(C_1-C_{30})$ alkyl-substituted phenyl ring, or a sorbitan fatty ester; $R_2$, $R_3$ and $R_4$ independently are $-H$ or $(C_1-C_{10})$ alkyl, aryl or alkylaryl; a is 0 or 1; b is 0 to 50; c is 0 to 150; d is 0 to 50; e is equal to or greater than 1 and X is a group containing at least one ethylenic double bond;
   b) about 10 to about 60% by weight $(C_3-C_{30})$ ethylenically-unsaturated, ionizable monomer, and
   c) about 0.1 to about 90% by weight nonionic $(C_2-C_{30})$ ethylenically-unsaturated monomer, and
   d) 0 to about 10% by weight multi-functional compounds;
2) said ionically-soluble polymer is physically or chemically attached to said polymer particle such that, upon neutralizing said ionically-soluble polymer with base or acid, at least a portion of said ionically-soluble polymer remains attached to the remainder of said polymer particle; and
3) said ionically-soluble polymer comprises from about 1% to about 99% by weight of said polymer particle.

The polymer particles are useful as improved thickeners and demonstrate improved viscosity stability to colorants, improved viscosity stability on heat-aging, improved early blister resistance, improved color float and improved syneresis resistance.

BACKGROUND OF THE INVENTION

Many pH-responsive thickeners are known in the art and are used to thicken water-based compositions. These thickeners are generally based upon the incorporation of a hydrophobic surfactant monomer into a hydrophilic, polymeric backbone. The traditional backbone composition for these thickeners primarily included monomeric acid, such as acrylic or methacrylic acid, and an alkyl acrylate or methacrylate, such as ethyl acrylate. The hydrophobic surfactant component is primarily derived from a polyethoxylated alkyl group. Several patents disclose pH-responsive thickeners and the various linkages connecting the hydrophobic surfactant component to the polymer backbone.

U.S. Pat. No. 4,384,096 discloses liquid emulsion polymers useful as pH-responsive thickeners containing an acrylate or methacrylate linkage. U.S. Pat. No. 4,569,965 discloses crotonatecontaining polymeric thickeners. U.S. Pat. No. 4,464,524 discloses polymer thickeners containing maleate linkages. U.S. Pat. No. 4,663,385 discloses copolymers of alkyl poly(oxyalkylene) itaconic diesters. U.S. Pat. No. 4,616,074 discloses acrylic-methylene succinic ester emulsion copolymers for thickening aqueous systems. U.S. Pat. No. 4,338,239 discloses thickener copolymers having allyl glycidyl ether linkages. U.S. Pat. No. 4,514,552 discloses alkali soluble latex thickeners containing urethane linkages. U.S. Pat. No. 4,600,761 discloses thickener copolymers containing isocyanato ethyl methacrylate linkages. European patent publication No. 0216479 discloses polymeric thickeners containing allyl ether linkages.

The polymeric thickeners of the prior art had several disadvantages which adversely affected their performance in paint applications. The disadvantages of the prior art thickeners were loss of viscosity upon heat-aging and colorant addition, decreased scrub resistance, and blistering over chalky substrates. The present invention overcomes nearly all these disadvantages of the prior art thickeners by providing multi-stage polymer particles wherein the ionically-soluble thickener copolymer (preferably base-soluble) has been physically or chemically attached (either directly or indirectly) to another (preferably base-insoluble) polymer stage. When the polymer particles of this invention are incorporated into water-containing compositions and neutralized with a base or acid, a portion of the ionically-soluble polymer stage remains attached to the remainder of the polymer particle.

Mixtures or blends of alkali-soluble polymers with alkali-insoluble polymers are known in the art, such as described in U.S. Pat. No. 3,037,952. Additionally, European Patent Publication No. 0207854 discloses a coating composition containing core-shell polymer particles containing (A) 95–99% by weight of at least one $C_1-C_8$ alkyl acrylate or methacrylate and (B) 1–5% by weight of at least one water soluble monomer. However, none of these references teach multi-stage polymer particles which are useful as thickeners comprising a hydrophobically-modified, ionically-soluble polymer stage.

DETAILED DESCRIPTION

This invention relates to novel polymer particles which are useful as thickeners. The polymer particles are useful in a variety of applications such as inks, adhesives, coatings, paints, pigment dispersants, textile thickeners, cosmetic formulations, oil well drilling fluids, liquid detergents and water treatment. The polymer particles of the present invention exhibit surprising improvements in viscosity stability upon addition of pre-dispersed colorants and upon heat-aging, and improvements in early blister resistance, color float and syneresis resistance.

The novel polymer particle of this invention comprises two or more polymer stages wherein:
1) at least one of said polymer stages is an ionically-soluble polymer, said ionically-soluble polymer being polymerized from a monomer mixture comprising;
   a) about 0.1 to about 55% by weight hydrophobic monomer having the formula;

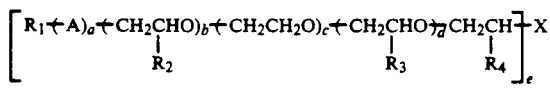

where A is
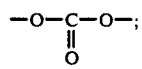
$-O-\overset{\underset{\parallel}{O}}{C}-O-$;

$R_1$ and $R_5$ independently are $(C_1-C_{30})$ alkyl, a (mono-, di-, or tri-) $(C_1-C_{30})$ alkyl-substituted phenyl ring, or a sorbitan fatty ester; $R_2$, $R_3$ and $R_4$ independently are —H or $(C_1-C_{10})$ alkyl, aryl or alkylaryl; a is 0 or 1; b is 0 to 50; c is 0 to 150; d is 0 to 50; e is equal to or greater than 1 and X is a group containing at least one ethylenic double bond;

b) about 10 to about 60% by weight $(C_3-C_{30})$ ethylenically-unsaturated, ionizable monomer, and c) about 0.1 to about 90% by weight nonionic $(C_2-C_{30})$ ethylenically-unsaturated monomer, and d) 0 to about 10% by weight multi-functional compounds;

2) said ionically-soluble polymer is physically or chemically attached to said polymer particle such that, upon neutralizing said ionically-soluble polymer with base or acid, at least a portion of said ionically-soluble polymer remains attached to the remainder of said polymer particle; and 3) said ionically-soluble polymer comprises from about 1% to about 99% by weight of said polymer particle.

Preferably said ionically-soluble polymer stage comprises from about 50% to about 95%, more preferably about 70% to about 90%, most preferably about 80%, by weight of said polymer particle.

Preferably said ionically-soluble polymer stage is base-soluble. More preferably the polymer particles of this invention comprise at least one base-soluble polymer stage and at least one base-insoluble polymer stage, wherein the weight ratio of said base-soluble polymer to said base-insoluble polymer is about 99:1 to about 1:99; more preferably about 95:5 to about 50:50.

Each of the polymer stages of the polymer particles of this invention is sequentially polymerized and, as used herein, the term "stage" refers to the polymer formed during each sequence of polymerization. Each stage is also defined as being different from the immediately proceeding and/or immediately subsequent stage by a difference of at least 0.1% by weight in monomer composition. The polymer particles may be prepared by a variety of processes which are well known in the art, such as suspension, emulsion, dispersion, bulk or solution polymerization. Preferably the multi-stage polymer particles of this invention are prepared by emulsion polymerization. Reference can be made to U.S. Pat. No. 4,427,836 (herein incorporated by reference) for specific process conditions.

The polymer particle preferably comprises at least one polymer stage which is base-insoluble and at least one polymer stage which is base-soluble. "Base-insoluble" as used herein means that the polymer is substantially insoluble in aqueous medium which has been adjusted with base to a pH of about 5.0 or greater. The base-insoluble stage has a particle size of 0.1 to about 5000 nanometers.

The composition of the polymer stages, other than said ionically-soluble stage, is not critical and can be of any polymeric composition. Preferably, the polymer particles have at least one base-insoluble polymer stage which is polymerized from a monomer mixture comprising about 1% to about 100% by weight monoethylenically-unsaturated monomer and about 0% to about 99% by weight multi-functional compounds (more preferably from about 70 to 99.9% by weight monoethylenically-unsaturated monomers and 0.1% to 30% by weight multi-functional compounds). More preferably, said mono-ethylenically-unsaturated monomers are selected from the group consisting of methyl acrylate, ethyl acrylate, butyl acrylate, 2-ethylhexyl acrylate, decyl acrylate, hydroxyethyl acrylate, hydroxypropyl acrylate, hydroxybutyl acrylate, methyl methacrylate, ethyl methacrylate, butyl methacrylate, hydroxyethyl methacrylate, hydroxypropyl methacrylate, hydroxybutyl methacrylate, acrylonitrile, methacrylonitrile, acrylic acid, methacrylic acid, itaconic acid, maleic acid, fumaric acid, crotonic acid, acrylic anhydride, methacrylic anhydride, maleic anhydride, itaconic anhydride, fumaric anhydride, styrene, substituted styrene, vinyl acetate, vinyl butyrate, vinyl caprolate, acrylamide, methacrylamide, butadiene, isoprene, vinyl chloride, vinylidene chloride, ethylene, propylene and other $C_1-C_{18}$ alkyl or hydroxyalkyl acrylates, methacrylates, fumarates, maleates or crotonates. The base-insoluble polymer stage can contain from about 0 to about 5% (based on weight of monomer) of chain transfer agents selected from the group consisting of alkyl-mercaptans such as dodecyl mercaptan, t-dodecyl mercaptan, octyl mercaptan, tetradecyl mercaptan, hexadecyl mercaptan and octadecyl mercaptan; hydroxyethyl mercaptan; mercaptopropionic acid; ethyl mercaptopropionate; methyl mercaptopropionate; butyl mercaptopropionate; thioglycolic acid; methyl thioglycolate; ethyl thioglycolate and butyl thioglycolate.

Multi-functional compounds as used herein means a) compounds having two or more sites of unsaturation; b) reactive chain transfer agents having two or more abstractable atoms; c) hybrid compounds having one or more sites of unsaturation and one or more abstractable atoms; d) amine-functional monomers that associate ionically with a base-soluble stage or; e) compounds having one or more sites of unsaturation and one or more nucleophilic or electrophilic reaction sites. Preferably the multi-functional compounds used to polymerize said base-insoluble polymer stage are selected from the group consisting of allyl-, methallyl-, vinyl-, and crotyl-esters of acrylic, methacrylic, maleic (mono-and di-esters), fumaric (mono-and di-esters), and itaconic (mono- and di-esters) acids; allyl-, methallyl-, and crotyl-vinyl ether and thioether; N-and N,N-di-allyl-methallyl-, crotyl-and vinyl-amides of acrylic and methacrylic acids; N-allyl-, methallyl-, and crotyl-maleimide; vinyl esters of 3-butenoic and 4-pentenoic acids; diallyl benzene, diallyl phthalate; triallyl cyanurate; O-allyl-, methallyl-, crotyl-, O-alkyl-, aryl-, P-vinyl-, P-allyl, P-crotyl-, and P-methallyl-phosphonates; triallyl-, trimethallyl-, and tricrotyl-phosphates; O-vinyl-, O, O-diallyl-, dimethallyl-, and dicrotyl-phosphates; cycloalkenyl esters of acrylic, methacrylic, maleic (mono-and di-esters), fumaric (mono- and di-esters), and itaconic (mono- and di-esters) acids [such as dicyclopentenyloxyethyl (meth) acrylate and dicyclopentenyl (meth) acrylate]; vinyl ethers and vinyl thioethers of cycloalkenols and cycloalkene thiols; vinyl esters of cycloalkene carboxylic acids; 1,3-butadiene, isoprene and other conjugated dienes; para-methylstyrene; chloromethylstyrene; allyl-, methallyl-, vinyl-, and crotyl-mercaptan; bromotrichloromethane; bromoform; carbon tetrachloride; carbon tetrabromide; N,N'-methylene-bis-acrylamide; ethylene glycol diacrylate; diethylene glycol diacrylate; triethylene glycol diacrylate; tetraethylene glycol diacrylate; polyethylene glycol diacrylate; polypropylene glycol diacrylate; butanediol diacrylate; hexanediol diacrylate; pentaerythritol triacrylate; trimethylolpropane triacrylate; tripropylene glycol diacrylate; neopentyl glycol diacrylate; ethylene glycol dimethacrylate; diethylene glycol dimethacrylate; triethylene glycol dimethacrylate; polyethylene glycol dimethacrylate; polypropylene glycol dimethacrylate; butanediol dimethacrylate; hexanediol dimethacrylate; trimethylolethane trimethacrylate; trimethylolpropane trimethacrylate; divinyl benzene; N,N-dimethylamino ethyl acrylate; N,N-dimethylamino ethyl methacrylate; N,N-diethylamino ethyl acrylate; N,N-diethylamino ethyl methacrylate; N-t-butylamino ethyl acrylate; N-t-butylamino ethyl methacrylate; N,N-dimethylamino propyl acrylamide; N,N-dimethylamino propyl methacrylamide; N,N-diethylamino propyl acrylamide; N,N-diethylamino propyl methacrylamide; p-aminostyrene, N,N-cyclohexylallylamine; 3-N,N-dimethylamino neopentyl acrylate; 3-N,N-dimethylamino neopentyl methacrylate; diallylamine; dimethallylamine; N-ethyl dimethallylamine; N-ethylmethallylamine; N-methyldiallylamine; 2-vinylpyridine; 4-vinylpyridine; glycidyl methacrylate; isocyanatoethyl methacrylate; alpha, alpha-dimethyl-m-isopropenyl benzyl isocyanate; chloroethyl acrylate; bromoethyl acrylate; iodoethyl acrylate; chloroethyl methacrylate; bromoethyl methacrylate and iodoethyl methacrylate.

It is critical to the practice of this invention that at least one of the polymer stages of the multi-stage polymer particle be an ionically-soluble polymer. Ionically-soluble means that the polymer is substantially soluble in water when ionized by pH adjustment or chemical reaction (such as quaternization). Ionically-soluble preferably means that the polymer is either acid-soluble or base-soluble as defined herein. The term "acid-soluble" as used herein means that the polymer is substantially soluble in an aqueous medium which has been adjusted with acid to a pH of about 9.0 or less. The term "base-soluble" as used herein means that the polymer is substantially soluble in an aqueous medium which has been adjusted with base to a pH of about 5.0 or greater. The term "ionically-insoluble" as used herein means that the polymer is not ionically-soluble as defined above.

The ionically-soluble polymer stage is polymerized from a monomer mixture comprising
a) about 0.1 to about 55% by weight hydrophobic monomer having the formula;

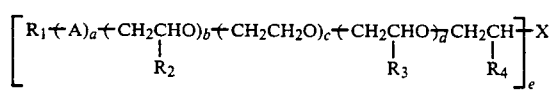

where A is —O—, —S—, —N—, —C—N—, —C—O— or
$\phantom{xx}$ $\phantom{x}$ $\phantom{xx}$ | $\phantom{xx}$ || | ||
$\phantom{xx}$ $\phantom{x}$ $\phantom{xx}$ R₅ $\phantom{xx}$ O R₅ $\phantom{xx}$ O

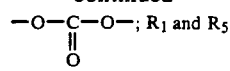

independently are (C₁-C₃₀) alkyl, a (mono-, di, or tri-) C₁-C₃₀ alkyl-substituted phenyl ring, or a sorbitan fatty ester; R₂, R₃ and R₄ independently are —H or (C₁-C₁₀) alkyl, aryl or alkylaryl; a is 0 or 1; b is 0 to 50; c is 0 to 150; d is 0 to 50; e is equal to or greater than 1 and X is a group containing at least one ethylenic double bond;

b) about 10 to about 60% by weight (C₃-C₃₀) ethylenically-unsaturated, ionizable monomer and;

c) about 0.1 to about 90% by weight nonionic (C₂-C₃₀) ethylenically-unsaturated monomer (i.e. containing no carboxylic acid functionality or other ionizable functionality), and d) 0 to about 10% by weight multi-functional compounds.

Preferably the monomer mixture for preparing the ionically-soluble polymer stage comprises about 2 to about 20% of said hydrophobic monomer. Preparation of hydrophobic monomer which can be used in this invention is described in many literature references, such as U.S. Pat. No. 4,075,411, which is herein incorporated by reference. In the above formula, X can be any group containing at least one ethylenic double bond, but preferably X is selected from the group consisting of acrylates, methacrylates, crotonates, maleates (mono- and di-esters), fumarates (mono- and di-esters), itaconates (mono- and di-esters), ethylenically-unsaturated urethanes, allyl ethers, methallyl ethers and vinyl ethers.

As previously mentioned, the ionically-soluble polymer stage can be either an acid-soluble polymer or a base-soluble polymer. The acid-soluble polymer stage comprises from about 10 to about 60% by weight (C₃-C₃₀) ethylenically unsaturated, ionizable monomers such as N,N-dimethylamino ethyl acrylate; N,N-dimethylamino ethyl methacrylate; N,N-diethylamino ethyl acrylate; N,N-diethylamino ethyl methacrylate; N-t-butylamino ethyl acrylate; N-t-butylamino ethyl methacrylate; N,N-dimethylamino propyl acrylamide; N,N-dimethylamino propyl methacrylamide; N,N-diethylamino propyl acrylamide; N,N-diethylamino propyl methacrylamide; p-aminostyrene; N,N-cyclohexylallylamine; 3-N, N-dimethylamino neopentyl acrylate; 3-N, N-dimethylamino neopentyl methacrylate; allylamine; diallylamine; dimethylallylamine; N-ethyl dimethallylamine; N-ethylmethallylamine; 2-vinylpyridine; 4-vinylpyridine; vinyl imidazole; crotyl amines and the like.

Preferably the ionically-soluble polymer stage is a base-soluble polymer wherein said (C₃-C₃₀) ethylenically-unsaturated, ionizable monomer is a carboxylic acid monomer.

The carboxylic acid monomer used in the polymerization of the base-soluble polymer stage preferably has the chemical formula:

$$R_6CH=C-COOH$$
$$\phantom{xxxxx}|$$
$$\phantom{xxxxx}R_7$$

where R₆ is —H, —CH₃ or COOY; R₇ is —H, (C₁-C₄) alkyl or —CH₂COOY; and Y is —H or (C₁-C₁₀) alkyl. Suitable carboxylic acid monomers include, for example, acrylic acid, methacrylic acid, itaconic acid, fumaric acid, maleic acid, crotonic acid and the like. The most preferred carboxylic acid monomer is methacrylic acid.

The nonionic ethylenically unsaturated monomers useful in this invention are preferably those having the chemical formula;

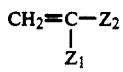

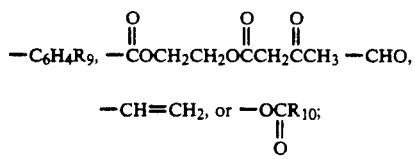

where $Z_1$ is —H, —$CH_3$ or Cl; $Z_2$ is —CN, —Cl, —$COOR_8$, $$-C_6H_4R_9, -\overset{O}{\underset{\|}{C}}OCH_2CH_2O\overset{O}{\underset{\|}{C}}CH_2\overset{O}{\underset{\|}{C}}CH_3 -CHO,$$

$$-CH=CH_2, \text{ or } -O\overset{}{\underset{\|}{C}}R_{10};$$
$$\quad\quad\quad\quad\quad\quad\quad O$$

$R_8$ is $C_1$-$C_{10}$ alkyl or $C_2$-$C_8$ hydroxyalkyl,
$R_9$ is —H, —Cl, —Br or $C_1$-$C_{10}$ alkyl; and $R_{10}$ is $C_1$-$C_{10}$ alkyl.

Examples of suitable nonionic ethylenically-unsaturated monomer are ethyl acrylate, butyl acrylate, methyl methacrylate, butyl methacrylate, 2-ethylhexyl acrylate, 2-hydroxyethyl acrylate, styrene, vinyl acetate, acrylonitrile, vinyl chloride and the like.

The multi-functional compounds which are useful in polymerizing said ionically-soluble polymer are selected from the group consisting of allyl-, methallyl-, vinyl-, and crotyl-esters of acrylic, methacrylic, maleic (mono-and di-esters), fumaric (mono- and di-esters), and itaconic (mono- and di-esters) acids; allyl-, methallyl-, and crotyl-vinyl ether and thioether; N- and N, N-diallyl, methallyl-, crotyl- and vinyl-amides of acrylic and methacrylic acids; N-allyl-, methallyl-, and crotyl-maleimide; vinyl esters of 3-butenoic and 4-pentenoic acids; diallyl benzene, diallyl phthalate; triallyl cyanurate; O-allyl-, methallyl-, crotyl-, O-alkyl-, aryl-, P-vinyl, P-allyl, P-crotyl, and P-methallyl-phosphonates; triallyl-, trimethallyl-, and tricrotyl-phosphates; O-vinyl, O,O-diallyl-, dimethallyl-, and dicrotyl-phosphates; cycloalkenyl esters of acrylic, methacrylic, maleic (mono- and di-esters), fumaric (mono- and di-esters), and itaconic (mono- and di-esters) acids; vinyl ethers and vinyl thioethers of cycloalkenols and cycloalkene thiols; vinyl esters of cycloalkene carboxylic acids; 1,3-butadiene, isoprene and other conjugated dienes; paramethylstyrene; chloromethylstyrene; allyl-, methallyl-, vinyl-, and crotylmercaptan; bromotrichloromethane; bromoform; carbon tetrachloride; carbon tetrabromide; N,N'-methylene-bis-acrylamide; ethylene glycol diacrylate; diethylene glycol diacrylate; triethylene glycol diacrylate; tetraethylene glycol diacrylate; polyethylene glycol diacrylate; polypropylene glycol diacrylate; butanediol diacrylate; hexanediol diacrylate; pentaerythritol triacrylate; trimethylolpropane triacrylate; tripropylene glycol diacrylate; neopentyl glycol diacrylate ethylene glycol dimethacrylate; diethylene glycol dimethacrylate; triethylene glycol dimethacrylate; polyethylene glycol dimethacrylate; polypropylene glycol dimethacrylate; butanediol dimethacrylate; hexanediol dimethacrylate; trimethylolethane trimethacrylate; trimethylolpropane trimethacrylate; divinyl benzene; glycidyl methacrylate; isocyanatoethyl methacrylate; alpha, alpha-dimethyl-m-isopropenyl benzyl isocyanate; chloroethyl acrylate; bromoethyl acrylate; iodoethyl acrylate; chloroethyl methacrylate; bromoethyl methacrylate and iodoethyl methacrylate.

Multi-functional compounds as used above means; a) compounds having two or more sites of unsaturation, b) reactive chain transfer agents having two or more abstractable atoms, c) hybrid compounds having one or more sites of unsaturation and one or more abstractable atoms; d) amine-functional monomers that associate ionically with a base-soluble stage; or e) compounds having one or more sites of unsaturation and one or more nucleophilic or electrophilic reaction sites.

The monomer mixture used to polymerize the ionically-soluble polymer can contain from about 0 to about 5% (based on the weight of said monomer mixture) of chain transfer agents selected from the group consisting of alkyl-mercaptans, such as dodecyl mercaptan, t-dodecyl mercaptan, octyl mercaptan, octyl decyl mercaptan, tetradecyl mercaptan and hexadecyl mercaptan; hydroxyethyl mercaptan; mercaptopropionic acid; methyl mercaptopropionate; ethyl mercaptopropionate; butyl mercaptopropionate; methyl thioglycolate; thioglycolic acid; ethyl thioglycolate and butyl thioglycolate.

In preparing the multi-stage polymer particles of the present invention, the ionically-insoluble polymer stage can be polymerized and subsequently the ionically-soluble polymer stage is polymerized in the presence of the ionically-insoluble polymer stage. Alternatively, the ionically-soluble polymer stage can be polymerized and subsequently the ionically-insoluble polymer stage is polymerized in the presence of the ionically-soluble polymer stage (i.e. inverse polymerization); due to the hydrophobicity of the ionically-insoluble polymer, it becomes one or more domains within the ionically-soluble polymer. A further technique for preparing the multi-stage polymer particles involves polymerization of the ionically-insoluble polymer stage, addition of multi-functional compounds which are allowed to soak into said ionically-insoluble polymer, polymerization of said multi-functional compounds, and subsequent polymerization of said ionically-soluble polymer stage.

The ionically-soluble polymer is physically or chemically attached to the polymer particle such that, upon neutralizing said ionically-soluble polymer (with either a base in the case of a base-soluble polymer or an acid in the case of an acid-soluble polymer) a significant portion (i.e. about 0.5% by weight or greater) of the ionically-soluble polymer remains attached to the remainder of the polymer particle. Physically or chemically attached as used herein means attachment by Van der Waals or London forces, ionic bonding, covalent bonding, hydrogen bonding, chain entanglement or any other means. Preferably the ionically-soluble polymer is chemically grafted to the polymer particle using one or more of the multi-functional compounds described below. Chemical grafting results in permanent attachment of a portion of the ionically-soluble polymer to the polymer particle and results in improved stability toward alcohols/solvents, colorants and other additives.

The following multi-functional compounds are useful to graft said ionically-soluble polymer stage to said ionically-insoluble polymer stage wherein said ionically-insoluble polymer stage is polymerized initially and said ionically-soluble polymer stage is subsequently polymerized: allyl-, methallyl-, vinyl, and crotyl-esters of acrylic, methacrylic, maleic (mono- and di-esters), fumaric (mono- and di-esters), and itaconic (mono- and di-esters) acids; allyl-, methallyl, and crotyl-vinyl ether and thioether; N- and N,N-di-allyl-, methallyl-, crotyl, and vinyl-amides of acrylic and methacrylic acids; N-allyl-, methallyl, and crotyl-maleimide; vinyl esters of 3-butenoic and 4-pentenoic acids; diallyl benzene, diallyl phthalate; triallyl cyanurate; O-allyl-,methallyl-, crotyl-, O-alkyl-, aryl-, P-vinyl-, P-allyl, P-crotyl-, and P-methallyl-phosphonates; triallyl-, trimethallyl-, and tricrotyl-phosphates; O-vinyl-, O,O-diallyl-, dimethallyl-, and dicrotyl-phosphates; cycloalkenyl esters of acrylic, methacrylic, maleic (mono-and di-esters), fumaric (mono- and di-esters), and itaconic (mono- and di-esters) acids; vinyl ethers and vinyl thioethers of cycloalkenols and cycloalkene thiols; vinyl esters of cycloalkene carboxylic acids; 1,3-butadiene, isoprene and other conjugated dienes; para-methylstyrene; chloromethylstyrene; allyl-, methallyl-, vinyl-, and crotyl-mercaptan; bromotrichloromethane; bromoform; carbon tetrachloride; carbon tetrabromide; glycidyl methacrylate; isocyanatoethel methacrylate; alpha, alpha-dimethyl-m-isopropenyl benzyl isocyanate; chloroethyl acrylate; bromoethyl acrylate; iodoethyl acrylate; chloroethyl methacrylate; bromoethyl methacrylate and iodoethyl methacrylate. The multi-functional compounds listed above are polymerized as part of and during the polymerization of said ionically-insoluble polymer stage.

The following multi-functional compounds are useful for grafting wherein said ionically-insoluble polymer stage is polymerized, followed by the addition of multi-functional compounds which are allowed to soak into said ionically-insoluble polymer, and subsequent sequential polymerization of said multi-functional compounds and said ionically-soluble polymer stage, respectively: N,N-methylene-bis-acrylamide; ethylene glycol diacrylate; diethylene glycol diacrylate; triethylene glycol diacrylate; tetraethylene glycol diacrylate; polyethylene glycol diacrylate; polypropylene glycol diacrylate; butanediol diacrylate; hexanediol diacrylate; pentaerythritol triacrylate; trimethylolpropane triacrylate; tripropylene glycol triacrylate; neopentyl glycol diacrylate; ethylene glycol dimethacrylate; diethylene glycol dimethacrylate; triethylene glycol dimethacrylate; polyethylene glycol dimethacrylate; polypropylene glycol dimethacrylate; butanediol dimethacrylate; hexanediol dimethacrylate; trimethylolethane trimethacrylate; trimethylolpropane trimethacrylate; divinyl benzene; allyl-, methallyl-, vinyl, and crotyl-esters of acrylic, methacrylic maleic (mono- and di-esters), fumaric (mono- and di-esters), and itaconic (mono- and di-esters) acids; allyl-, methallyl, and crotyl-vinyl ether and thioether; N-and N, N-di-allyl-, methallyl-, crotyl-, and vinyl-amides of acrylic and methacrylic acids; N-allyl-, methallyl, and crotyl-maleimide; vinyl esters of 3-butenoic and 4-pentenoic acids; diallyl benzene, diallyl phthalate; triallyl cyanurate; O-allyl-, methallyl-, crotyl-, O-alkyl-, aryl-, P-vinyl-, P-allyl, P-crotyl-, and P-methallyl-phosphonates; triallyl-, trimethallyl-, and tricrotyl-phosphates; O-vinyl-, O, O-diallyl-, dimethallyl-, and dicrotyl-phosphates; cycloalkenyl esters of acrylic, methacrylic, maleic (mono- and di-esters), fumaric (mono-and di-esters), and itaconic (mono- and di-esters) acids; vinyl ethers and vinyl thioethers of cycloalkenols and cycloalkene thiols; vinyl esters of cycloalkene carboxylic acids; 1,3-butadiene, isoprene and other conjugated dienes; glycidyl methacrylate; isocyanatoethyl methacrylate; alpha, alpha-dimethyl-m-isopropenyl benzyl isocyanate; chloroethyl acrylate; bromoethyl acrylate; iodoethyl acrylate; chloroethyl methacrylate; bromoethyl methacrylate; iodoethyl methacrylate.

The following multi-functional compounds are useful for grafting wherein said ionically-soluble polymer stage is initially polymerized along with said multi-functional compounds and subsequently said ionically-insoluble polymer stage is polymerized (inverse polymerization): allyl-, methallyl-, vinyl, and crotylesters of acrylic, methacrylic, maleic (mono- and di-esters), fumaric (mono- and di-esters), and itaconic (mono- and di-esters) acids; allyl-, methallyl, and crotylvinyl ether and thioether; N- and N,N-di-allyl-, methallyl-, crotyl, and vinylamides of acrylic and methacrylic acids; N-allyl-, methallyl, and crotylmaleimide; vinyl esters of 3-butenoic and 4-pentenoic acids; diallyl benzene, diallyl phthalate; triallyl cyanurate; O-allyl-, methallyl-, crotyl-, O-alkyl-, aryl-, P-vinyl-, P-allyl-, P-crotyl-, and P-methallyl-phosphonates; triallyl-, trimethallyl-, and tricrotyl-phosphates; O-vinyl-, O, O-diallyl-, dimethallyl-, and dicrotyl-phosphates; cycloalkenyl esters of acrylic, methacrylic, maleic (mono -and di-esters), fumaric (mon- and di-esters), and itaconic (mono- and di-esters) acids; vinyl ethers and vinyl thioethers of cycloalkenols and cycloalkene thiols; vinyl esters of cycloalkene carboxylic acids; 1, 3-butadiene, isoprene and other conjugated dienes; paramethylstyrene; chloromethylstyrene; allyl-, methallyl-, vinyl-, and crotyl-mercaptan; bromotrichloromethane; bromoform; carbon tetrachloride and carbon tetrabromide. The following multi-functional compounds are useful for grafting wherein said ionically-soluble stage is initially polymerized and subsequently said ionically-insoluble stage is polymerized along with said multi-functional compounds (inverse polymerization); N,N-dimethylamino ethyl acrylate; N,N-diethylamino ethyl methacrylate; N,N-diethylamino ethyl acrylate; N,N-diethylamino ethyl methacrylate; N-t-butylamino ethyl acrylate; N-t-butylamino ethyl methacrylate; N,N-dimethylamino propyl acrylamide; N,N-dimethylamino propyl methacrylamide; N,N-diethylamino propyl acrylamide; N, N-diethylamino propyl methacrylamide; p-aminostyrene; N,N-cyclohexylallylamine; 3-N,N-dimethylamino neopentyl acrylate; 3-N, N-dimethylamino neopentyl methacrylate; diallylamine; dimethallylamine; N-ethyl dimethallylamine; N-ethylmethallylamine; N-methyldiallylamine; 2-vinylpyridine; 4-vinylpyridine. The multi-functional compounds listed below are useful for grafting wherein said ionically-soluble stage is initially polymerized and subsequently said ionically-insoluble stage is polymerized (inverse polymerization). These multi-functional compounds can be polymerized in either said ionically-soluble or ionically-insoluble stages; glycidyl methacrylate; isocyanatoethyl methacrylate; alpha, alpha-dimethyl-m-isopropenyl benzyl isocyanate; chloroethyl acrylate; bromoethyl acrylate; iodoethyl acrylate; chloroethyl methacrylate; bromoethyl methacrylate; iodoethyl methacrylate.

The most preferred multi-functional compounds for grafting in the inverse polymerization techniques are the crotyl-esters of acrylic, methacrylic, maleic (mono- and di-esters), fumaric (mono- and di-esters), and itaconic (mono- and di-esters) acids (such as crotyl methacrylate); crotyl-vinyl ether and thioether; N-di-crotylamides of acrylic and methacrylic acids; N-crotylmaleimide; O-crotyl-, P-crotyl-phosphonates; tricrotylphosphates; dicrotyl-phosphates; cycloalkenyl esters of acrylic, methacrylic, maleic (mono- and di-esters), fumaric (mono- and di-esters), and itaconic (mono- and di-esters) acids (such as dicyclopentenyloxyethylmethacrylate, dicyclopentenyl acrylate, dicyclopentenyl methacrylate); vinyl ethers and vinyl thioethers of cycloalkenols and cycloalkene thiols; vinyl esters of cycloalkene carboxylic acids; and crotylmercaptan. The multi-functional compounds listed above are polymerized as part of and during the polymerization of said ionically-soluble polymer stage.

The polymer particles of this invention are useful in a wide variety of applications as described earlier. The polymer particles are useful either in dried form or as an emulsion of the polymer particles in an aqueous medium. The polymer particles are preferably used as an aqueous emulsion composition or added to water-containing compositions wherein in either case the ionically-soluble polymer is neutralized and substantially dissolved with either a base or an acid; except that a portion of said ionically-soluble polymer remains attached or associated with the insoluble polymer stage(s). Based on equivalents of carboxylic acid in the base-soluble polymer, preferably about 0.8 to about 1.5 equivalents of base are introduced to said compositions to neutralize the base-soluble polymer. The neutralized base-soluble polymer is dissolved in the aqueous medium, but a significant portion remains attached to the remainder of the polymer particle.

The base used to neutralize said base-soluble polymer can be any, but is preferably selected from the group consisting of ammonium hydroxide, potassium hydroxide, sodium hydroxide, lithium hydroxide, triethylamine, triethanolamine, monoethanolamine, 2-amino-2-methyl-1-propanol and dimethylaminoethanol.

The polymer particles are useful in a method of thickening water-containing compositions (preferably containing about 20% by weight water or greater) by incorporating the polymer particles therein and neutralizing. The base-soluble polymer is neutralized with base by adjusting the pH of the compositions to about 5.0 or greater. The acid-soluble polymer is neutralized with acid by adjusting the pH of the composition to about 9.0 or less. The amount of the polymer particles used as a thickener depends upon the particular application, but is generally used in an amount of from about 0.1% to about 20% by weight of the total composition. The compositions to be thickened using the polymer particles of this invention can contain many additional ingredients such as pigments, fillers, extenders, surfactants, stabilizers, biocides and the like.

The following examples are presented to demonstrate this invention. The examples are intended in an illustrative, but not limitative, sense. All parts and percentages are by weight unless otherwise indicated. The following abbreviations are used in the Examples:

| | |
|---|---|
| BA = | butyl acrylate |
| MMA = | methyl methacrylate |
| ALMA = | allyl methacrylate |
| MAA = | methacrylic acid |
| EA = | ethyl acrylate |
| MA-20 = | methacrylate ester of a 20 mole ethoxylate of cetylstearyl alcohol |
| A-103 = | disodium ethoxylated nonyl phenol half ester of sulfosuccinic acid |
| BMP = | butyl mercaptopropionate |
| D.I. water = | deionized water |
| CrMA = | crotyl methacrylate |
| CPS = | centipoise |
| DPH = | diallyl phthalate |
| Q-1 = | dicyclopentenyloxyethyl methacrylate |
| BMA = | butyl methacrylate |

-continued

| | |
|---|---|
| ST = | styrene |
| Q-2 = | methacrylate ester of a 23 mole ethoxylate of lauryl alcohol |
| LMA = | lauryl methacrylate |
| TMI-970 = | alpha, alpha-dimethyl-m-isopropenyl benzyl isocyanate adduct with 50 mole ethoxylate of nonyl phenol |
| Cr-20 = | crotyl ester of a 20 mole ethoxylate of cetyl-stearyl alcohol |
| Al-20 = | allyl ester of a 20 mole ethoxylate of cetyl-stearyl alcohol |
| TMI-20 = | alpha, alpha-dimethyl-m-isopropenyl benzyl isocyanate adduct with a 20 mole ethoxylate of cetylstearyl alcohol. |

EXAMPLE 1

An emulsion of polymer particles within the scope of this invention was prepared as follows:

A stirred reactor containing 1,532 g. of deionized (D.I.) water, and 9 g. of 28 wt % sodium lauryl sulfate solution (in water) was heated to 80° C. under nitrogen. Next, 42 g. of monomer emulsion (M.E.) #1, shown below, was added to the reactor followed by 0.95 g. of ammonium persulfate dissolved in 35 g. of D.I. water, and a 24 g. D.I. water rinse. After 10 minutes, the remainder of M.E. #1 and cofeed #1 (shown below) was added to the reactor over a 30-minute period while maintaining the reactor temperature at 80° C. A 47 g. D.I. water rinse was used to flush the feed lines and the water added to the reactor. After a 10 minute hold (at 80° C.), a solution of 0.45 g. of ammonium persulfate, 1.9 g. of a 33 wt % solution of A-103 (in water), and 70 g. of D.I. water was added to the reactor over a 10-minute period. Next M.E. #2 (shown below) and cofeed #2 (shown below) was added to the reactor over a 210-minute time period. The temperature was maintained at 80° C. throughout the additions. At the end of the feeds the monomer emulsion feed lines were flushed with 48 g. of D.I. water and the water added to the reactor. After a 30-minute hold (at 80° C.) the dispersion was cooled.

The final product had a solids content of 32.5%, Brookfield viscosity of 7 centipoises (cps), and a pH of 3.1. When 6.2 g. of this material was mixed with 0.7 g. of 50 wt % NaOH and 193.1 g of D.I. water the resulting mixture had a viscosity of 102 cps (Brookfield viscometer, 30 rpm). When 12.3 g. of this material was mixed with 1.4 g of 50 wt % NaOH and 186.3 g. of D.I. water the resulting mixture had a Brookfield viscosity of 4,620 cps (30 rpm).

| | (BASE-INSOLUBLE) STAGE | (BASE-SOLUBLE) STAGE |
|---|---|---|
| | M.E. #1 | M.E. #2 |
| D.I. water | 91.0 g | 495.0 g |
| Sodium lauryl sulfate (28 wt %) | 10.8 g | — |
| A-103 (33 wt % in water) | — | 33.3 g |
| BA | 142.5 g | — |
| MMA | 95.0 g | — |
| ALMA | 7.5 g | — |
| MAA | 5.0 g | 428.0 g |
| EA | — | 500.0 g |
| MA-20 (70 wt % solution in MAA) | — | 71.5 g |
| BMP | — | .6 g |
| | COFEED #1 | COFEED #2 |
| D.I. water | 35.0 | 150.0 g |

|  | (BASE-INSOLUBLE) STAGE | (BASE-SOLUBLE) STAGE |
| --- | --- | --- |
| Ammonium Persulfate | .2 g | 1.1 g |

EXAMPLES 2A-B

Ex. 2A

An emulsion of polymer particles within the scope of this invention was prepared as follows:

A stirred reactor containing 650 g. of D.I. water, and 3.8 g. of 28 wt % sodium lauryl sulfate solution (in water) was heated to 83° C. under nitrogen. Next, 18 g. of monomer emulsion (M.E.) #1, shown below, was added to the reactor followed by 0.4 g. of ammonium persulfate dissolved in 15 g. of D.I. water, and a 10 g. D.I. water rinse. After 5 minutes, the remainder of M.E. #1 and cofeed #1 (shown below) was added to the reactor over a 40-minute period while maintaining the reactor temperature at 83° C. A 20 g. D.I. water rinse was used to flush the feed lines and the water added to the reactor. After a 10-minute hold (at 83° C.), the reactor was cooled to 81° C. and a solution of 0.2 g. of ammonium persulfate, 0.8 g. of a 33 wt. % solution of A-103 (in water), and 30 g. of D.i. water was added to the reactor over a 5 minute period. Next M.E. #2 (shown below) and cofeed #2 (shown below) were added to the reactor over a 200 minute time period. The temperature was maintained at 81° C. throughout the additions. At the end of the feeds, the monomer emulsion feed lines were flushed with a 20 g. of D.I. water and the water added to the reactor. After a 30-minute hold (at 81° C.) the dispersion was cooled.

The final product has a solids content of 32.4%, Brookfield viscosity of 11 cps, and a pH of 3.0. When 12.4 g. of this material was mixed with 1.4 g. of 50 wt. % NaOH and 186.3 g. of D.I. water the resulting mixture had a viscosity of 72 cps (Brookfield viscometer, 30 rpm).

|  | M.E. #1 | M.E. #2 |
| --- | --- | --- |
| D.I. Water | 38.5 g. | 195.0 g. |
| Sodium lauryl sulfate (28 wt %) | 4.5 g. | — |
| A-103 (33 wt % in water) | — | 14.1 g. |
| BA | 70.5 g. | — |
| MMA | 30.2 g. | — |
| MAA | 2.1 g. | 181.9 g. |
| ALMA | 3.2 g. | — |
| EA | — | 211.8 g. |
| MA-20 (70 wt % solution in MAA) | — | 22.7 g. |
| Q-2 (70 wt % solution in MAA) | — | 7.6 g. |
| BMP | — | .3 g. |
|  | COFEED #1 | COFEED #2 |
| D.I. Water | 20.0 g. | 78.0 g. |
| Ammonium Persulfate | .1 g. | .5 g. |

Ex. 2B

An emulsion of polymer particles within the scope of this invention was prepared as in Ex. 2A above, except that in monomer Emulsion #1 the amount of BA, MMA and ALMA was changed to 62.3 grams, 41.6 grams and 0.0 grams, respectively. The final product has a solids content of 32.0%, Brookfield viscosity of 9 cps and a pH of 3.0 of this material was mixed with 0.7 of 50 wt. % NaOH and 96.3 g. of D.I. water, the resulting mixture had a Brookfield (30 rpm) viscosity of 380 cps.

EXAMPLE 3 A-B(Comparative)

Emulsions of polymer particles falling outside the scope of this invention were prepared using conventional emulsion polymerization techniques utilizing the following recipe:

| Example 3A |  |
| --- | --- |
|  | Monomer Emulsion |
| D.I. water | 650.0 g. |
| Sodium lauryl sulfate (28% soln) | 35.0 g. |
| EA | 625.0 g. |
| MA-20 (70 wt % solution in MAA) | 89.3 g. |
| MAA | 535.7 g. |
| BMP | .8 g. |
|  | COFEED |
| D.I. Water | 150.0 g. |
| Ammonium Persulfate | 1.0 g. |
| Example 3B |  |
|  | Monomer Emulsion |
| D.I. water | 600.0 g. |
| A-103 (33 wt % in water) | 35.2 g. |
| MA-20 (70 wt % solution in MAA) | 56.8 g. |
| Q-2 (70 wt % solution in MAA) | 18.9 g. |
| MAA | 454.3 g. |
| BMP | .7 g. |
| EA | 530.0 g. |
|  | COFEED |
| D.I. water | 88.0 g. |
| Ammonium Persulfate | .9 g. |

The final product from Ex. 3A has a solids content of 32.0%, Brookfield (30 rpm) viscosity of 11 cps, and a pH of 2.8. The final product from Ex. 3B had a solids content of 33.1%, Brookfield viscosity of 12 cps (30 rpm) and a pH of 3.7.

EXAMPLE 4 (Comparative)

An emulsion of polymer particles falling outside the scope of this invention was prepared using conventional emulsion polymerization techniques utilizing the following recipe:

|  | MONOMER EMULSION |
| --- | --- |
| D.I. Water | 192.3 g. |
| Sodium lauryl sulfate (28 wt %) | 22.7 g. |
| BA | 302.1 g. |
| MMA | 201.4 g. |
| MAA | 10.6 g. |
| ALMA | 15.9 g. |
|  | COFEED |
| D.I. Water | 98.0 g. |
| Ammonium Persulfate | .4 g. |

The final product had a solids content of 39.1%, Brookfield viscosity of 24 cps, and a pH of 2.5.

EXAMPLE 5 (Comparative)

A composition falling outside the scope of this invention was prepared by mixing 1000 grams of the sample prepared in Ex. 3B and 211 grams of the sample prepared in Ex. 4. The resulting mixture had a solids content of 34.4.%, Brookfield viscosity of 13 centipoises and a pH of 3.65. When 5.8 grams of this product was mixed with 1.4 grams of 50 wt. % NaOH and 192.8 grams of D.I. water, the resulting mixture had a viscosity of 58 centipoise (Brookfield viscometer, 30 rpm).

EXAMPLES 6-10

Various compositions within the scope of this invention were prepared following the procedures of Ex. 1. All of the compositions comprised polymer particles having a base-soluble 2nd stage polymer comprising 50% ethyl acrylate, 45% methacrylic acid, 5% MA-20, and 0.063% butyl mercaptopropionate based on weight of 2nd stage monomers. The compositions of the 1st stage polymer are presented in Table I below. The weight ratio of 2nd stage polymer to 1st stage polymer was 80:20.

TABLE I

| Example | Composition of 1st Stage Polymer (%) | | | |
|---|---|---|---|---|
| | BA | MMA | ALMA | MAA |
| 6 | 58 | 39 | 3 | 0 |
| 7 | 52 | 35 | 3 | 10 |
| 8 | 46 | 31 | 3 | 20 |
| 9 | 28 | 19 | 3 | 50 |
| 10 | 22 | 15 | 3 | 60 |

EXAMPLES 11-14

Various compositions within the scope of this invention were prepared as in Examples 6-10, except that the 1st stage polymer of the polymer particles had the compositions given in Table II.

TABLE II

| Example | Composition of 1st Stage Polymer (%) | | | |
|---|---|---|---|---|
| | BA | MMA | ALMA | MAA |
| 11 | 59 | 39 | 0 | 2 |
| 12 | 53 | 35 | 10 | 2 |
| 13 | 47 | 31 | 20 | 2 |
| 14 | 41 | 27 | 30 | 2 |

EXAMPLES 15-23

Various compositions within the scope of this invention were prepared as in Examples 6-10, except that the 1st stage polymer of the polymer particles had the compositions given in Table III.

TABLE III

| Example | Composition of 1st Stage Polymer (%) | | | | | |
|---|---|---|---|---|---|---|
| | BA | MMA | CRMA | Q-1 | DPH | MAA |
| 15 | 58 | 39 | 1 | — | — | 2 |
| 16 | 57 | 38 | 3 | — | — | 2 |
| 17 | 56 | 37 | 5 | — | — | 2 |
| 18 | 53 | 35 | 10 | — | — | 2 |
| 19 | 47 | 31 | 20 | — | — | 2 |
| 20 | 57 | 38 | — | 3 | — | 2 |
| 21 | 53 | 35 | — | 10 | — | 2 |
| 22 | 57 | 38 | — | — | 3 | 2 |
| 23 | 53 | 35 | — | — | 10 | 2 |

EXAMPLES 24-30

Various compositions within the scope of this invention were prepared following the procedures of Ex. 1. The 2nd stage polymer of the polymer particle comprised 50% ethyl acrylate, 45% methacrylic acid, 5% MA-20 and 0.063% BMP based on weight of 2nd stage monomer. The compositions of the 1st stage polymer are presented in Table IV below. The weight ratio of 2nd stage polymer to 1st stage polymer was 80:20.

TABLE IV

| Example | Composition of 1st Stage Polymer (%) |
|---|---|
| 24 | 95 ethyl hexyl acrylate/3 allyl methacrylate/2 methacrylic acid |
| 25 | 95 styrene/3 allyl methacrylate/2 methacrylic acid |
| 26 | 95 ethyl acrylate/3 allyl methacrylate/2 methacrylic acid |
| 27 | 95 butyl methacrylate/3 allyl methacrylate/2 methacrylic acid |
| 28 | 48 hydroxyethyl methacrylate/47 butyl acrylate/3 allyl methacrylate/2 methacrylic acid |
| 29 | 57.2 butyl acrylate/38.1 methyl methacrylate/3 allyl methacrylate/1.7 acrylic acid |
| 30 | 56.4 butyl acrylate/37.6 methyl methacrylate/3 allyl methacrylate/3.0 itaconic acid |

EXAMPLES 31-42

Various compositions within the scope of this invention were prepared following the procedures of Ex. 1, except that the 1st stage polymer comprised 57% butyl acrylate, 38% methyl methacrylate, 3% allyl methacrylate and 2% methacrylic acid; and the 2nd stage polymer had compositions as shown in Table V below. The weight ratio of 2nd stage polymer to 1st stage polymer was 80:20. The 2nd stage polymer also contained 0.063% butyl mercaptopropionate, except for Ex. 34 wherein the 2nd stage polymer contained 0.047% methyl mercaptopropionate.

TABLE V

| Example | Composition of 2nd Stage Polymer (%) | | | | | | |
|---|---|---|---|---|---|---|---|
| | EA | MAA | MMA | BA | BMA | ST | MA-20 |
| 31 | 85 | 10 | — | — | — | — | 5 |
| 32 | 75 | 20 | — | — | — | — | 5 |
| 33 | 65 | 30 | — | — | — | — | 5 |
| 34 | 50 | 45 | — | — | — | — | 5 |
| 35 | 35 | 60 | — | — | — | — | 5 |
| 36 | 52 | 45 | — | — | — | — | 3 |
| 37 | 45 | 45 | — | — | — | — | 10 |
| 38 | 15 | 45 | — | — | — | — | 40 |
| 39 | 25 | 45 | 25 | — | — | — | 5 |
| 40 | 25 | 45 | — | 25 | — | — | 5 |
| 41 | 25 | 45 | — | — | 25 | — | 5 |
| 42 | 25 | 45 | — | — | — | 25 | 5 |

EXAMPLES 43-48

Various compositions within the scope of this invention were prepared following the procedures in Ex. 1, except that the 1st stage polymer comprised 57% butyl acrylate, 38% methyl methacrylate, 3% allyl methacrylate and 2% methacrylic acid; and the 2nd stage polymer had compositions as shown in Table VI below. The 2nd stage polymer also contained 0.063% butyl mercaptopropionate. The weight ratio of 2nd stage polymer to 1st stage polymer was 80:20.

TABLE VI

| Example | Composition of 2nd Stage Polymer (%) | | | | | | | |
|---|---|---|---|---|---|---|---|---|
| | EA | MAA | LMA | Q-2 | TMI-970 | Cr-20 | Al-20 | TMI-20 |
| 43 | 49.7 | 45 | — | 5.3 | — | — | — | — |
| 44 | 44.0 | 45 | — | — | 11 | — | — | — |
| 45 | 53.9 | 45 | 1.1 | — | — | — | — | — |
| 46 | 50 | 45 | — | — | — | 5 | — | — |

TABLE VI-continued

| Example | Composition of 2nd Stage Polymer (%) | | | | | | | |
|---|---|---|---|---|---|---|---|---|
| | EA | MAA | LMA | Q-2 | TMI-970 | Cr-20 | Al-20 | TMI-20 |
| 47 | 50.1 | 45 | — | — | — | — | 4.9 | — |
| 48 | 49.4 | 45 | — | — | — | — | — | 5.6 |

EXAMPLES 48-54

Compositions within the scope of this invention were prepared following the procedures of Ex. 1, except that the weight ratio of 1st stage polymer to 2nd stage polymer was changed as shown in Table VII below.

TABLE VII

| Example | (weight ratio) | |
|---|---|---|
| | 1st Stage Polymer | 2nd Stage Polymer |
| 49 | 1 | 99 |
| 50 | 5 | 95 |
| 51 | 10 | 90 |
| 52 | 30 | 70 |
| 53 | 70 | 30 |
| 54 | 90 | 10 |

EXAMPLE 55

An emulsion of polymer particles within the scope of this invention was prepared as follows:

A stirred reactor containing 1,533 g. of D.I. water, and 28 g. of 28 wt % sodium lauryl sulfate solution (in water) was heated to 80° C. under nitrogen. Next, 42 g. of monomer emulsion (M.E.) #1 shown below, was added to the reactor followed by 0.95 g. of ammonium persulfate dissolved in 35 g. of D.I. water, and a 25 g. D.I. water rinse. After 10 minutes, the remainder of M.E. #1 and cofeed #1 (shown below) was added to the reactor over a 210-minute period while maintaining the reactor temperature at 80° C. A 48 g. D.I. water rinse was used to flush the feed lines and the water added to the reactor. After a 10-minute hold (at 80° C.), a solution of 0.45 g. of ammonium persulfate, 1.9 g. of a 33 wt % solution of A-103 (in water), and 70 g. of D.I. water was added to the reactor over a 10-minute period. Next M.E. #2 (shown below) and cofeed #2 (shown below) was added to the reactor over a 30-minute time period. The temperature was maintained at 80° C. throughout the additions. At the end of the feeds the monomer emulsion feed lines were flushed with 47 g. of D.I. water and the water added to the reactor. After a 30-minute hold (at 80° C.) the dispersion was cooled.

The final product has a solids content of 33.8%, viscosity of 10 cps, and a pH of 2.5. When 5.9 g. of this material was mixed with 0.7 g of 50 wt % NaOH and 193.4 g. of D.I. water the resulting mixture had a viscosity of 824 cps (Brookfield viscometer, 30 rpm). When 11.8 g. of this material was mixed with 1.4 g. of 50 wt % NaOH and 186.8 g. of D.I. water the resulting mixture had a Brookfield viscosity of 10,840 cps (30 rpm).

| | (BASE-SOLUBLE) STAGE | (BASE-INSOLUBLE) STAGE |
|---|---|---|
| | M.E. #1 | M.E. #2 |
| D.I. water | 495.0 g. | 90.0 g. |
| Sodium lauryl sulfate (28 wt %) | 28.0 g. | 10.8 g. |
| EA | 497.5 g. | — |
| MA-20 (70 wt % solution in MAA) | 71.4 g. | — |
| MAA | 428.6 g. | — |
| CrMa | 2.5 g. | — |
| BMP | .6 g. | — |
| BA | — | 150.0 g. |
| MMA | — | 100.0 g. |
| | COFEED #1 | COFEED #2 |
| D.I. water | 150.0 g. | 48.0 g. |
| Ammonium Persulfate | 1.1 g. | .2 g. |

EXAMPLE 56

An emulsion of polymer particles within the scope of this invention was prepared as follows:

A 1st stage polymer was prepared following the procedures of Example 1, but using the monomer emulsion [M.E.] #1 described below. Next, the reactor was cooled to 60° C. and 30 g. of 1,3 butylene dimethacrylate added. After stirring for about 10 minutes, solutions of 0.53 g. t-butyl hydroperoxide in 7 g. D.I. water, 0.27 g. sodium sulfoxylate formaldehyde in 8 g. D.I. water, and 2 g. of 0.15 wt % ferrous sulfate heptahydrate were added to the reactor. The temperature rose from 60° to 61° C. After 30 minutes the reactor was heated to 80° C., and a solution of 0.45 g. of ammonium persulfate, 1.9 g. of a 33 wt % solution of A-103 [in water], and 70 g. of D.I. water was added to the reactor over a 10-minute period. Next M.E. #2 [shown below] and cofeed #2 [shown below] was added to the reactor over a 210-minute time period. The temperature was maintained at 80° C. throughout the additions. At the end of the feeds the monomer emulsion feed lines were flushed with 48 g. of D.I. water and the water added to the reactor. After a 30-minute hold at 80° C. the dispersion was cooled.

The final product had a solids content of 32.7% and a Brookfield viscosity of 7 cps. When 6.1 g. of this material was mixed with 0.7 g. of 50 wt % NaOH and 193.2 g. of D.I. water the resulting mixture had a viscosity of 680 cps (Brookfield viscometer, 30 rpm). When 12.2 g. of this material was mixed with 1.3 g. of 50 wt % NaOH and 186.5 g. of D.I. water the resulting mixture had a Brookfield viscosity of 11,360 cps (30 rpm).

| | (BASE-INSOLUBLE) STAGE | (BASE-SOLUBLE) STAGE |
|---|---|---|
| | M.E. #1 | M.E. #2 |
| D.I. water | 91.0 g. | 495.0 g. |
| Sodium lauryl sulfate (28 wt %) | 10.8 g. | — |
| A-103 (33 wt % in water) | — | 33.3 g. |
| BA | 147.5 g. | — |
| MMA | 97.5 g. | — |
| MAA | 5.0 g. | 428.6 g. |
| EA | — | 500.0 g. |
| MA-20 (70 wt % solution in MAA) | — | 71.4 g. |
| | Cofeed #1 | Cofeed #2 |

|  | (BASE-INSOLUBLE) STAGE | (BASE-SOLUBLE) STAGE |
|---|---|---|
| D.I. water | 48.0 g. | 150.0 g. |
| Ammonium Persulfate | .2 g. | 1.1 g. |

EXAMPLES 57–60 (Comparative)

Various emulsions of single-stage polymer particles falling outside the scope of this invention were prepared following the procedures of Example 3, but having the following compositions:

| Ex. | COMPOSITION (%) | | | | | | | |
|---|---|---|---|---|---|---|---|---|
|  | EA | MAA | MMA | MA-20 | MMP | BMP | CrMA | TMI-970 |
| 57 | 25 | 45 | 25 | 5 | — | 0.063 | — | — |
| 58 | 44 | 45 | — | — | — | 0.063 | — | 11.0 |
| 59 | 49.75 | 45 | — | 5 | — | 0.063 | 0.25 | — |
| 60 | 50 | 45 | — | 5 | 0.047 | — | — | — |

EXAMPLE 61

Emulsions of polymer particles within the scope of this invention were each formulated into a paint composition as a thickener using the following recipe:

| GRIND: Ingredient | Amount (parts by weight) |
|---|---|
| Propylene glycol | 70.00 |
| Hydrophillic acrylic dispersant | 12.00 |
| Defoamer | 1.0 |
| Water | 45.0 |
| Titanium dioxide | 210.0 |
| Clay | 88.0 |
| Let Down: | |
| Water | 50.0 |
| Acrylic binder | 378.0 |
| Ester-alcohol coalescent | 11.4 |
| Defoamer | 3.0 |
| Biocide | 2.0 |
| Ammonium hydroxide | 1.8 |
| Thickener/water | 201.0 |

Each paint composition was thickened using a sufficient amount of the polymer particles (on a dry weight basis) to give an initial viscosity of about 85 Kreb Units (KU) at a pH of about 9.5 adjusted with ammonium hydroxide. After sitting for a period of 3–5 days, the paint composition was sheared by mixing for 5 minutes and the equilibrium viscosity measured. Comparative compositions were prepared using the same formulation above but incorporating as thickeners the emulsions prepared in comparative examples 3B and 5. The compositions were evaluated for viscosity stability after heat-aging, viscosity stability upon colorant addition and early blister resistance.

The viscosity stability after heat-aging was measured by subjecting approximately 250 grams of the paint composition to storage in a ½ pint paint can at 60° C. for 10 days. The paint samples were then cooled to room temperature, sheared by mixing for 5 minutes, and viscosity measured. The difference between the viscosity of the heat-aged samples and the equilibrium viscosity is presented in Table VIII below.

Viscosity stability upon colorant addition was evaluated by measuring the viscosity decline which occurred after addition of the equivalent of 8 ounces of pthalo blue colorant to a gallon of each paint composition. This data is presented in Table VIII below.

Early blister resistance was evaluated following ASTM method D659-86 and D-714 by applying two coats of each paint composition to a chalky acrylic substrate with a 6-hour drying time between coats at 77° F. and 50% relative humidify. After drying overnight, the substrates were subjected to a mist of deionized water and the formation of blister defects were rated over time. The results are presented in Table VIII below (0=worst, 10=best, F=few, M=medium, MD=medium dense, D=dense).

TABLE VIII

| Sample | Thickener/ Amount (lbs/gal.) | Viscosity Stability (KU) | | Early Blister Resistance | | |
|---|---|---|---|---|---|---|
|  |  | Heat-Aging | Colorant addition | 0.5 hrs. | 1.0 hrs. | 2.0 hrs. |
| A | Ex. 2A 3.53 | −7 | −7 | 7D | 6M | 3M |
| B | Ex. 2B 2.82 | −9 | −9 | 8F | 6M | 4M |
| C* | Ex. 3B 2.68 | −16 | −12 | 7D | 6D | 3D |
| D* | Ex. 5 3.08 | −14 | −13 | 7MD | 6D | 6D |

*comparative

The above data demonstrates that samples A and B within the scope of this invention have improved viscosity stability after heat-aging and upon colorant addition when compared to a single-stage thickener (sample C) and a blend of a single-stage thickener and an acrylic emulsion polymer (sample D). The comparative samples C and D showed nearly twice the viscosity loss of samples A and B. The data also shows that samples A and B exhibit equivalent early blister resistance relative to the comparative samples, despite the higher levels of thickener used in Samples A and B. It is generally known in the art that increasing the level of water-sensitive materials such as thickeners can be disadvantageous for early blister resistance.

EXAMPLE 62

Emulsions of polymer particles within the scope of this invention were formulated into paint compositions and evaluated following the procedures of Example 61. Corresponding comparative formulations were also prepared using emulsions of single-stage polymer particles falling outside the scope of this invention. The results are presented in Table IX.

TABLE IX

| Sample | Thickener/Amount (lbs/gal.) | Viscosity Stability (KU) Heat-Aging | Viscosity Stability (KU) Colorant addition | Early Blister Resistance 0.5 hrs. | Early Blister Resistance 1.0 hrs. | Early Blister Resistance 2.0 hrs. |
|---|---|---|---|---|---|---|
| E  | Ex. 1/3.47  | −2  | −8  | 7MD | 6MD | 4MD |
| F* | Ex. 3A/2.00 | −16 | −15 | 7MD | 6M  | 4MD |
| G  | Ex. 39/3.79 | −8  | −14 | 6D  | 5D  | 3D  |
| H* | Ex. 57/2.14 | −11 | −14 | 7D  | 6D  | 5D  |
| I  | Ex. 34/2.92 | +1  | −9  | 7MD | 6D  | 5D  |
| J* | Ex. 60/2.10 | −14 | −11 | 7MD | 6D  | 5D  |
| K  | Ex. 44/2.98 | +5  | −11 | 6MD | 5D  | 3D  |
| L* | Ex. 58/2.10 | −13 | −14 | 7MD | 6D  | 5D  |
| M  | Ex. 55/2.52 | +2  | −8  | 8MD | 7MD | 6MD |
| N* | Ex. 59/1.90 | −12 | −12 | 8MD | 8MD | 7D  |

*comparative

EXAMPLE 63

An emulsion of polymer particles falling within the scope of this invention was prepared as follows:

A stirred reactor containing 600 g. of D.I. water, and 5.2 g. of 42 wt % amphoteric surfactant (Abex-1404, in water) was heated to 60° C. under nitrogen. Then 3.44 g. of 1 wt % versene solution and 3.44 g. of a 0.15 wt % ferrous sulfate heptahydrate solution was added to the reactor. A charge of 16.8 g. of monomer emulsion (M.E.) #1, shown below, was added to the reactor followed by 0.4 g. of ammonium persulfate dissolved in 40 g. of D.I. water, and a 10 g. D.I. water rinse. After 25 minutes, the remainder of M.E. #1, the cofeed initiator #1, and the cofeed reductant #1 (shown below) were added to the reactor over a 210 minute period while maintaining the reactor temperature at 60° C. A 19 g. D.I. water rinse was used to flush the feed lines and the water added to the reactor. After a 30 minute hold (at 60° C.), a solution of 0.12 g. of sodium sulfoxylate formaldehyde in 8 g. of D.I. water was added to the reactor and the temperature increased to 80° C. M.E. #2 (shown below) and cofeed #2 (shown below) were then added to the reactor over a 30 minute time period. The temperature was maintained at 80° C. throughout the additions. At the end of the feeds the monomer emulsion feed lines were flushed with 19 g. of D.I. water and the water added to the reactor. After a 30 minute hold (at 80° C.) the dispersion was cooled to room temperature.

The final product had a solids content of 28.4% and a Brookfield viscosity of 516 cps. When 35.2 g of this material was mixed with 2.5 g. of concentrated hydrochloric acid and 162.3 g. of D.I. water, the resulting mixture had a Brookfield viscosity of 728 cps (30 rpm).

|  | M.E. #1 | M.E. #2 |
|---|---|---|
| D.I. water | 198.0 g. | 36.0 g. |
| Amphoteric surfactant (Abex-1404, 42 wt % in water)* | 10.0 g. | 1.16 g. |
| EA | 119.6 g. | — |
| TMI-20 | 20.0 g. | — |
| Dimethyl aminoethylmethacrylate | 160.0 g. | — |
| CrMA | 0.4 g. | — |
| BA | — | 60.0 g. |
| MMA | 100.0 g. | 40.0 g. |

|  | Cofeed initiator #1 | Cofeed #2 |
|---|---|---|
| D.I. water | 80.0 g. | 20.0 g. |
| Ammonium Persulfate | 0.4 g. | .2 g. |

|  | Cofeed reductant #1 |
|---|---|
| D.I. water | 40.0 g. |

| Sodium sulfoxylate formaldehyde | 0.2 g. |
|---|---|

*Abex is a registered trademark of Alcolac, Inc.

We claim:

1. Polymer particle comprising two or more polymer stages wherein
   (a). the outermost stage of said polymer stages is ionically-soluble polymer, said ionically-soluble polymer being polymerized from a monomer mixture comprising:
      (1) about 0.1 to about 55% by weight hydrophobic monomer having the formula;

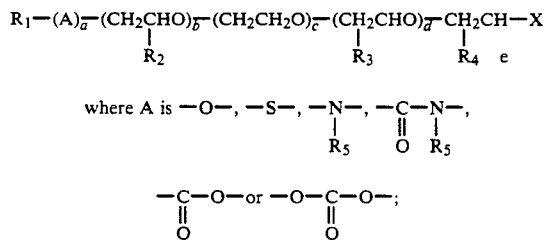

where $R_1$ and $R_5$ independently are $(C_1-C_{30})$ alkyl, a (mono-, di-, or tri-) $(C_1-C_{30})$ alkyl-substituted phenyl ring, or a sorbitan fatty ester; $R_2$, $R_3$ and $R_4$ independently are —H or $(C_1-C_{10})$ alkyl, aryl or alkylaryl; a is 0 or 1; b is 0 to 50; c is 0 to 150; d is 0 to 50; e is equal to or greater than 1 and X is a group containing at least one ethylenic double bond;

(2) about 10 to about 60% by weight $(C_3-C_{30})$ ethylenically-unsaturated, ionizable monomer, and
      (3) about 0.1 to about 90% by weight nonionic $(C_2-C_{30})$ ethylenically-unsaturated monomer and
      (4) 0 to about 10% by weight multifunctional compounds;
   (b). said ionically-soluble polymer is physically or chemically attached to said polymer particle such that, upon neutralizing said ionically-soluble polymer with base or acid, at least a portion of said ionically-soluble polymer remains attached to the remainder of said polymer particle; and
   (c). said ionically-soluble polymer comprises from about 1% to about 99% by weight of said polymer particle.

2. Polymer particle of claim 1 wherein said ionically-soluble polymer stage is base-soluble.

3. Polymer particle of claim 2 wherein all other of said polymer stages is a base-insoluble polymer, and the weight ratio of said base-insoluble polymer to said base-soluble polymer is about 1:99 to about 99:1.

4. Polymer particle of claim 2 wherein the weight ratio of said base-insoluble polymer to said base-soluble polymer is about 5:95 to about 50:50.

5. Polymer particle of claim 2 wherein said base-insoluble polymer is polymerized from a monomer mixture comprising about 1% to about 100% by weight monoethylenically-unsaturated monomer and about 0% to about 99% by weight multi-functional compounds.

6. Polymer particle of claim 5 wherein said monomer mixture of said base-insoluble polymer comprises about 70% to about 99.9% by weight monoethylenically-unsaturated monomer and about 0.1% to about 30% by weight multi-functional compounds.

7. Polymer particle of claim 5 wherein said monomer mixture of said base-insoluble polymer is selected from the group consisting of methyl acrylate, ethyl acrylate, butyl acrylate, 2-ethylhexyl acrylate, decyl acrylate, hydroxyethyl acrylate, hydroxypropyl acrylate, hydroxybutyl acrylate, methyl methacrylate, ethyl methacrylate, butyl methacrylate, hydroxyethyl methacrylate, hydroxypropyl methacrylate, hydroxybutyl methacrylate, acrylonitrile, methacrylonitrile, acrylic acid, methacrylic acid, itaconic acid, maleic acid, fumaric acid, acrylic anhydride, methacrylic anhydride, maleic anhydride, itaconic anhydride, fumaric anhydride, styrene, substituted styrene, vinyl acetate, vinyl butyrate, vinyl caprylate, acrylamide, methacrylamide, butadiene, isoprene, vinyl chloride, vinylidene chloride, ethylene, propylene and other $C_1$ to $C_{18}$ alkyl or hydroxyalkyl acrylates, methacrylate, fumarates, maleates or crotonates.

8. Polymer particle of claim 5 wherein said base-insoluble polymer contains multifunctional compounds selected from the group consisting of allyl-, methallyl-, vinyl-, and crotylesters of acrylic, methacrylic, maleic (mono- and di-esters), fumaric (mono- and di-esters), and itaconic (mono- and diesters) acids; allyl-, methallyl-, and crotyl-vinyl ether and thioether; N- and N,N-di-allyl-, methallyl-, crotyl-, and vinylamides of acrylic and methacrylic acids; N-allyl-, methallyl-, and crotyl-maleimide; vinyl esters of 3-butenoic and 4-pentenoic acids; diallyl benzene, diallyl phthalate; triallyl cyanurate; O-allyl-, methallyl-, crotyl-, O-alkyl-, aryl-, P-vinyl, P-allyl, P-crotyl-, and P-methallyl-phosphonates; triallyl-, trimethallyl-, and tricrotyl-phosphates; O-vinyl-, O, O-diallyl-, dimethallyl-, and dicrotyl-phosphates; cycloalkenyl esters of acrylic, methacrylic, maleic (mono- and di-esters), fumaric (mono- and di-esters), and itaconic (mono- and di-esters) acids; vinyl ethers and vinyl thioethers of cycloalkenols and cycloalkene thiols; vinyl esters of cycloalkene carboxylic acids; 1,3-butadiene, isoprene and other conjugated dienes; para-methylstyrene; chloromethylstyrene; allyl-, methallyl-, vinyl-, and crotyl-mercaptan; bromotrichloromethane; bromoform; carbon tetrachloride; carbon tetrabromide; N,N'-methylene-bis-acrylamide; ethylene glycol diacrylate; diethylene glycol diacrylate; triethylene glycol diacrylate; tetraethylene glycol diacrylate; polyethylene glycol diacrylate; polypropylene glycol diacrylate; butanediol diacrylate; hexanediol diacrylate; pentaerythritol triacrylate; trimethylolpropane triacrylate; tripropylene glycol diacrylate; neopentyl glycol diacrylate; ethylene glycol dimethacrylate; diethylene glycol dimethacrylate; triethylene glycol dimethacrylate; polyethylene glycol dimethacrylate; polypropylene glycol dimethacrylate; butanediol dimethacrylate; hexanediol dimethacrylate; trimethylolethane trimethacrylate; trimethylolpropane trimethacrylate; divinyl benzene; N,N-dimethylamino ethyl acrylate; N,N-dimethylamino ethyl methacrylate; N,N-diethylamino ethyl acrylate; N,N-diethylamino ethyl methacrylate; N-t-butylamino ethyl acrylate; N-t-butylamino ethyl methacrylate; N,N-dimethylamino propyl acrylamide; N,N-dimethylamino propyl methacrylamide; N,N-diethylamino propyl acrylamide; N,N-diethylamino propyl methacrylamide; p-aminostyrene; N,N-cyclohexylallylamine; 3-N,N-dimethylamino neopentyl acrylate; 3-N,N-dimethylamino neopentyl methacrylate; diallylamine; dimethylallyalmine; N-ethyl dimethallylamine; N-ethylmethallylamine; N-methyldiallylamine; 2-vinylpyridine; 4-vinylpyridine; glycidyl methacrylate; isocyanatoethyl methacrylate; alpha, alphadimethyl-m-isopropenyl benzyl isocyanate; chloroethyl acrylate; bromoethyl acrylate; idoethyl acrylate; chloroethyl methacrylate; bromoethyl methacrylate and idoethyl methacrylate.

9. Polymer particle of claim 1 wherein X is selected from the group consisting of acrylates, methacrylates, crotonates, maleates, fumarates, itaconates, ethylenically-unsaturated urethanes, allyl ethers, methallyl ethers and vinyl ethers.

10. Polymer particle of claim 1 wherein said multi-functional compounds are selected from the group consisting of allyl-, methallyl-, vinyl-, and crotyl-esters of acrylic, methacrylic, maleic (mono- and di-esters), fumaric (mono- and di-esters), and itaconic (mono- and di-esters) acids; allyl-, methallyl-, and crotyl-vinyl ether and thioether; N- and N,N-di-allyl-, methallyl-, crotyl- and vinyl-amides of acrylic and methacrylic acids; N-allyl-, methallyl-, and crotyl-maleimide; vinyl esters of 3-butenoic and 4-pentenoic acids; diallyl benzene, diallyl phthalate; triallyl cyanurate; O-allyl-, methallyl-, crotyl-, O-alkyl-, aryl-, P-vinyl, P-allyl, P-crotyl-, and P-methallyl-phosphonates; triallyl-, trimethallyl-, and tricrotyl-phosphates; O-vinyl-, O,O-diallyl-, dimethallyl-, and dicrotyl-phosphates; cycloaklenyl esters of acrylic, methacrylic, maleic (mono- and di-esters), fumaric (mono-and di-esters), and itaconic (mono- and di-esters) acids; vinyl ethers and vinyl thioethers of cycloalkenols and cycloalkene thiols; vinyl esters of cycloalkene carboxylic acids; 1,3-butadiene, isoprene and other conjugated dienes; para-methylstyrene; chloromethylstyrene; allyl-methallyl-, vinyl-, and crotyl-mercaptan; bromotrichloromethane; bromoform; carbon tetrachloride; carbon tetrabromide; N,N'-methylene-bis-acrylamide; ethylene glycol diacrylate; diethylene glycol diacrylate; triethylene glycol diacrylate; tetraethylene glycol diacrylate; polyethylene glycol diacrylate; polypropylene glycol diacrylate; butanediol diacrylate; hexanediol diacrylate; pentaerythritol triacrylate; trimethylolpropane triacrylate; tripropylene glycol diacrylate; neopentyl glycol diacrylate; ethylene glycol dimethacrylate; diethylene glycol dimethacrylate; triethylene glycol dimethacrylate; polyethylene glycol dimethacrylate; polypropylene glycol dimethacrylate; butanediol dimethacrylate; hexanediol dimethacrylate; trimethylolethane trimethacrylate; trimethylolpropane trimethacrylate; divinyl benzene; glycidyl methacrylate; isocyanatoethyl metharylate; alpha, alphadimethyl-m-isopropenyl benzyl isocyanate; chloroethyl acrylate; bromoethyl acrylate; idoethyl acrylate;

chloroethyl methacrylate; bromoethyl methacrylate and iodoethyl methacrylate.

11. Polymer particle of claim 1 wherein said ionizable monomer has the chemical formula:

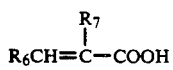

where $R_6$ is —H, —$CH_3$, or —COOY; $R_7$ is —H, $C_1$-$C_4$ alkyl, or —$CH_2$COOY; Y is —H or $C_1$-$C_{10}$ alkyl.

12. Polymer particle of claim 11 wherein said ionizable monomer is methacrylic acid.

13. Polymer particles of claim 1 wherein said nonionic ethylenically unsaturated monomer has the chemical formula:

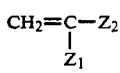

where $Z_1$ is —H, —$CH_3$ or Cl; $Z_2$ is —CN, —Cl,

—COO$R_8$, —$C_6H_4R_9$, —CHO, —C$R_8$,

—OC$R_{10}$; $R_8$ is $C_1$-$C_{10}$ alkyl or $C_2$-$C_8$ hydroxylalkyl;

$R_9$ is —H, —Cl, Br or $C_1$-$C_{10}$ alkyl; and $R_{10}$ is $C_1$-$C_{10}$ alkyl.

14. Polymer particle of claim 2 wherein said base-soluble polymer is prepared from a monomer mixture comprising about 2 to about 20% by weight of said hydrophobic monomer.

15. Polymer particles of claim 1 wherein said monomer mixture contains from about 0 to about 5%, based on the weight of said monomer mixture, of chain transfer agents selected from the group consisting of dodecyl mercaptan; t-dodecyl mercaptan; octyl mercaptan; tetradecyl mercaptan; octadecyl mercaptan; hexadecyl mercaptan; hydroxyethyl mercaptan; mercaptopropionic acid; methyl mercaptopropionate; ethyl mercaptopropionate; butyl mercaptopropionate; thioglycolic acid; methyl thioglycolate; ethyl thioglycolate and butyl thioglycolate.

16. Polymer particle of claim 2 wherein said base-insoluble polymer and said base-soluble polymer are emulsion polymerized.

17. Polymer particle of claim 16 wherein said base-insoluble polymer stage is polymerized and subsequently said base-soluble polymer stage is polymerized in the presence of said base-insoluble polymer stage.

18. Polymer particle of claim 16 wherein said base-soluble polymer stage is polymerized and subsequently said base-insoluble polymer stage is polymerized in the presence of said base-soluble polymer stage and, due to the hydrophobicity of said base-insoluble polymer, it becomes one or more domains within said base-soluble polymer.

19. A composition comprising an aqueous emulsion of the polymer particles of claim 2.

20. A composition of claim 19 wherein said base-soluble polymer has been neutralized and substantially dissolved with a base such that a portion of said base-soluble polymer remains attached to the remainder of said polymer particle.

21. A composition of claim 20 wherein said base is selected from the group consisting of ammonium hydroxide, potassium hydroxide, sodium hydroxide, lithium hydroxide, triethylamine, triethanolamine, monoethanolamine, 2-amino-2-methyl-1-propanol and dimethylaminoethanol.

22. A composition of claim 20 wherein the pH of said composition is about 5.0 or greater.

* * * * *